(12) United States Patent
Formenti et al.

(10) Patent No.: US 9,808,433 B2
(45) Date of Patent: Nov. 7, 2017

(54) COMBINATION OF A CENTRALLY-ACTING ANALGESIC AND A SELECTIVE CYCLOOXYGENASE-2 INHIBITOR ANTI-INFLAMMATORY AGENT FOR THE TREATMENT OF INFLAMMATION AND PAIN IN THE VETERINARY FIELD

(75) Inventors: Andrea Formenti, Milan (IT); Filippo Formenti, Milan (IT)

(73) Assignee: FORMEVET S.R.L., Milan (IT)

( * ) Notice: Subject to any disclaimer, the term of this patent is extended or adjusted under 35 U.S.C. 154(b) by 353 days.

(21) Appl. No.: 13/580,437

(22) PCT Filed: Feb. 17, 2011

(86) PCT No.: PCT/EP2011/052325
§ 371 (c)(1),
(2), (4) Date: Aug. 22, 2012

(87) PCT Pub. No.: WO2011/104161
PCT Pub. Date: Sep. 1, 2011

(65) Prior Publication Data
US 2012/0316232 A1    Dec. 13, 2012

(30) Foreign Application Priority Data
Feb. 26, 2010   (IT) .............................. MI2010A0318

(51) Int. Cl.
*A01N 57/10*   (2006.01)
*A61K 31/66*   (2006.01)
*A61K 31/137*   (2006.01)
*A61K 31/341*   (2006.01)

(52) U.S. Cl.
CPC .......... *A61K 31/137* (2013.01); *A61K 31/341* (2013.01)

(58) Field of Classification Search
CPC ..................................................... A61K 31/137
USPC ........................................................... 514/473
See application file for complete search history.

(56) References Cited

U.S. PATENT DOCUMENTS

| 2005/0090517 A1* | 4/2005 | Norris ........................... 514/282 |
| 2007/0020335 A1* | 1/2007 | Chen et al. ................... 424/486 |
| 2008/0027011 A1 | 1/2008 | Nached et al. |
| 2008/0220079 A1* | 9/2008 | Chen et al. ................... 424/490 |

FOREIGN PATENT DOCUMENTS

WO    2007/135505 A2    11/2007

OTHER PUBLICATIONS

Sarathchandra et al. "Ligation of the caudal mesenteric artery during resection and anastomosis of the colorectal junction for annular adenocarcinoma in two dogs." Australian veterinary journal 87.9 (2009): 356-359.*
Johnston, S., et al. "Nonsurgical Management of Osteoarthritis in Dogs," Vet. Clin. Small Anim. 38, 1449-1470 (2008).

* cited by examiner

*Primary Examiner* — Layla Soroush
(74) *Attorney, Agent, or Firm* — Silvia Salvadori, P.C.; Silvia Salvadori

(57) ABSTRACT

The present invention relates to veterinary pharmaceutical compositions for the treatment of pain and inflammation, containing a combination of Tramadol and Firocoxib, for oral administration.

5 Claims, 1 Drawing Sheet

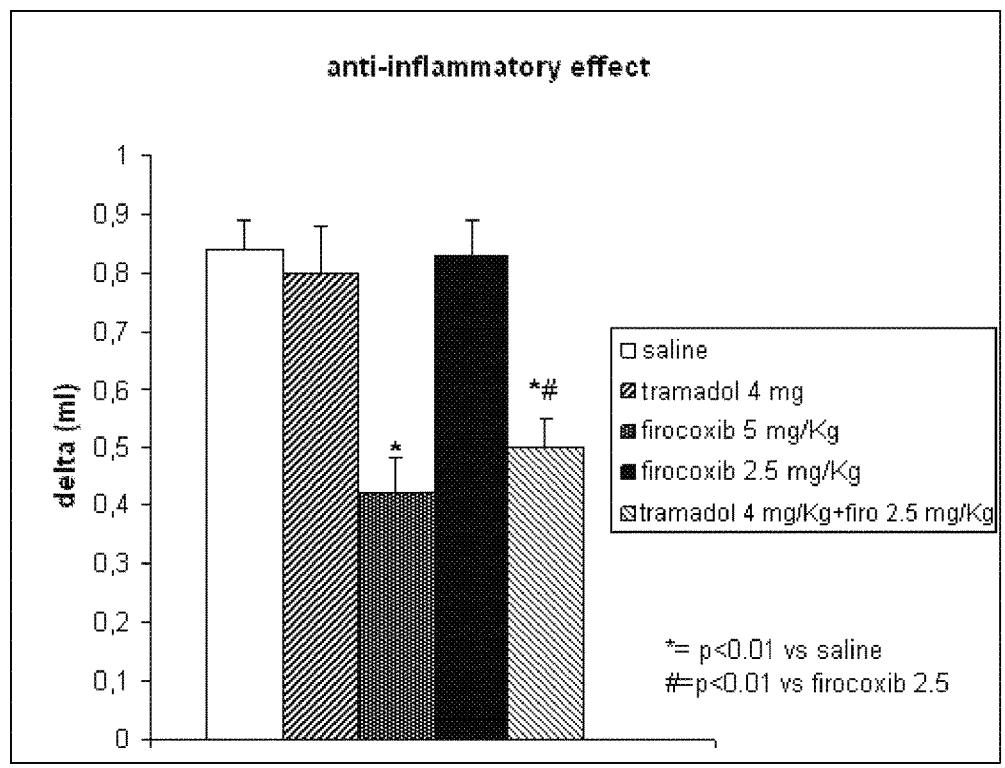
Mean ± SD of 8-10 rats
*= p<0.01 vs saline
# = p<0.01 vs NSAIDs
ANOVA + Bonferroni's t-test for multiple comparisons

COMBINATION OF A CENTRALLY-ACTING ANALGESIC AND A SELECTIVE CYCLOOXYGENASE-2 INHIBITOR ANTI-INFLAMMATORY AGENT FOR THE TREATMENT OF INFLAMMATION AND PAIN IN THE VETERINARY FIELD

This application is a U.S. national stage of PCT/EP2011/052325 filed on Feb. 17, 2011 which claims priority to and the benefit of Italian Application No. MI2010A000318 filed on Feb. 26, 2010, the contents of which are incorporated herein by reference.

FIELD OF INVENTION

The present invention relates to veterinary pharmaceutical compositions for the treatment of pain and inflammation, containing a combination of:
 a) Tramadol, and
 b) Firocoxib.

INTRODUCTION

Thanks to the progress of veterinary medicine, correct diet, improvements in hygienic conditions and the greater attention devoted to them, the life expectancy of animals, especially pets, has considerably increased, with the result that the occasions when animals perceive pain have multiplied.

For example, the current life expectancy of a well-cared-for cat or dog is at least 15 years. Inevitably, any animal becomes increasingly liable to health problems as it ages. The problems associated with aging are often accompanied by a more or less intense manifestation of pain which, if underestimated or neglected, has adverse effects on the quality of life of both the animal and its owner. The growing attention paid by owners to their animals reduces as far as possible the onset and symptoms correlated with a variety of disorders, whether associated with normal aging processes or resulting from the environmental influences affecting animals in their everyday lives.

Animals can suffer from disorders involving all organs and systems, i.e. both soft tissues (muscular system, digestive system, reproductive system, respiratory system, urinary system, integumentary system, nervous system, visual and auditory system) and hard tissues (skeleton). The disorders may be more or less characterised by inflammatory processes, but always involve more or less intense pain.

One of the most common disorders which can arise in both young and elderly animals is joint disease, which can affect any joint. The joint diseases that affect animals can be degenerative (osteoarthritis) or inflammatory (arthritis), both of which feature progressively worsening pain symptoms and a chronic inflammatory state or acute attacks.

While the presence of osteoarthritis/arthritis in elderly animals due to senility is normal, increasingly exaggerated selection criteria designed to accentuate certain characteristics of a breed have led to the appearance of degenerative joint disease even in young animals. This is the case with canine hip dysplasia. Hip dysplasia is a hereditary disorder which causes abnormal positioning of the hip joint, and progressively worsening osteoarthritis symptoms soon appear. In young dogs, the onset of the disease is usually manifested by pain of the rear limbs and a consequent reduction in physical activity (functio laesa). These pups have difficulty in getting up, going up stairs and running, and often have a jerky gait, etc.

Dogs, like humans, can also suffer from disorders of the spinal column. For example, the morphological characteristics of the basset hound, which were developed by selection so that the dog can hunt in burrows, have made its spinal column vulnerable, with considerable pain symptoms.

Pain, whether acute or chronic, represents one of the main causes of deterioration in the quality of the life for animals as well as humans.

Recognising its gravity and impact on the animal's life means being able to suggest the most suitable treatments and, by alleviating its suffering, ensure its general well-being. Pain must be treated in animals firstly to eliminate it as a symptom, and secondly because it adversely effects the whole body (by reducing food and fluid intake, causing aggression or depression, reducing mobility, promoting ankylosis, muscle atrophy and reduced gastrointestinal activity, delaying and jeopardising the body's healing process, etc.). Pain can be manifested as a single symptom or as a consequence of an acute or chronic inflammatory state. The action on both symptoms, with suitable monitoring, can therefore lead to more lasting therapeutic success.

The diagnosis, prognosis and treatment always begin with close observation of the animal's behaviour by the owner, followed by the involvement of the veterinary surgeon. The latter provides precise instructions about the correct management of the sick animal, and can prescribe the most suitable treatment using veterinary active ingredients/medicaments or, if none are available, use human medicaments.

The medicaments normally used for these treatments belong to the category of anti-inflammatories and/or analgesics, which do not always have a favourable risk/benefit ratio at present.

PRIOR ART

Non-steroidal anti-inflammatory drugs (NSAIDs) are one of the classes of drugs most commonly used in current out-patient practice to treat inflammation and pain.

From the pharmacokinetic standpoint, NSAIDs tend to be well absorbed by the oral route; their bioavailability varies from species to species, and food can reduce the oral absorption of some NSAIDs. There are also considerable differences in the elimination rate between different animal species.

One of the main limitations of their use is the appearance of side effects, mainly affecting the gastrointestinal tract, kidneys, haemostatic system, etc.

Their action mechanism involves reducing the production of important mediators of the inflammatory process, especially prostaglandins, by inhibiting the activity of the enzyme cyclooxygenase (COX) which catalyses their synthesis.

At least two types of COX, called COX-1 and COX-2, to which different functions are attributed, were identified in the 1990s.

COX-1 is physiologically present in the body, performing various protective functions at gastrointestinal and renal level, etc.; COX-2 seems not to be normally present in the cells, except in some particular areas, but its synthesis appears to be induced by the inflammatory process.

Inhibition of the two isoforms of COX (COX-1 and COX-2) at therapeutic doses can cause serious side effects in the digestive apparatus, the haemopoietic system and the kidneys, which means that its use in medium/long-term treatments is inadvisable.

In recent years, there has therefore been a move towards the use of new-generation anti-inflammatories which, being selective COX-2 inhibitors, show a significant reduction in the gastroenteric side effects typical of COX-1 inhibiting NSAIDs (although it is still recommended that they should not be administered to animals with gastrointestinal disorders or bleeding). Selective COX-2 inhibitors are still particularly contraindicated for animals with liver, heart or kidney function disorders or clotting disorders.

Firocoxib is a member of the category of non-steroidal anti-inflammatory drugs (NSAIDs) belonging to the coxib group, which act by selectively inhibiting COX-2. It has been demonstrated that in the dog, low therapeutic doses of this medicament do not significantly inhibit COX-1, while at high doses, the medicament can lose its selectivity.

Opioids are a group of drugs with central analgesic activity, which are used to treat moderate to severe pain.

According to the state of the art, Tramadol can be defined as a centrally-acting analgesic, which promotes its antinociceptive action through interaction with the receptor sites located along the descending pain pathways, and combines rapid activity with fewer and less serious side effects than other opioids, such as morphine.

Tramadol performs its pharmacological activity through a dual action mechanism, documented by numerous in vitro and in vivo studies, which has led international pain experts to define it as an "atypical opioid". The synergic action of Tramadol is based on:
  a selective interaction for the central opioid receptors (especially g) with a weak affinity having no physiological significance towards the other opioid receptors
  inhibition of noradrenaline reuptake at synaptic level and increased serotonin concentrations at central synaptic level.

Tramadol combines an effective, rapid analgesic action with a satisfactory profile of global tolerability. When administered at therapeutic doses, Tramadol does not depress the respiration, possesses good cardiovascular tolerability, does not act on the gastrointestinal tract, and does not induce tolerance or dependence.

Tramadol can therefore be considered a first-choice medicament for the treatment of acute and chronic painful states of various types and causes, of moderate or severe intensity (e.g. post-operative orthopaedic or gynaecological pain, etc.).

The pharmacokinetic profile of Tramadol indicates:
  very good absorption after oral administration, regardless of the formulation used
  peak plasma concentration within 2 hours
  low bond with plasma proteins
  elimination half-life of 1.5-7 hours.

Elimination mainly takes place through the renal route, and minimally through the faecal route.

DESCRIPTION OF THE INVENTION

It has now been found that the combination of Tramadol and Firocoxib is highly effective in the treatment of pain and inflammation in domestic animals.

The present invention therefore relates to veterinary pharmaceutical compositions for the treatment of inflammation and pain, containing a combination of:
  Tramadol, and
  Firocoxib.

More specifically, the present invention relates to compositions based on a combination of Tramadol and Firocoxib for the treatment of inflammation and pain in dogs, cats, horses, caged birds, rodents, lagomorphs, mustelids, ruminants and swine. The compositions according to the invention will contain variable doses of the active ingredients, depending on the animal for which they are intended. In any event, the doses of Firocoxib for each animal species will be lower than those conventionally used in treatments not combined with Tramadol, because they will be boosted by the presence of Tramadol and can be determined from time to time, on the basis of the doses used in the rat, suitably adapting them according to the different sensitivities of animals to treatment with anti-COX2 NSAIDs, bearing in mind that higher therapeutic doses of anti-inflammatories are needed in rats than for other mammals. In any event, these doses will still be lower than those normally used in treatment with Firocoxib alone. Broadly speaking, the doses of Firocoxib will be at least 10% lower, preferably 20%, more preferably 30% and even more preferably at least 40 to 50% lower than the doses conventionally used in treatments not combined with Tramadol.

Indicatively, in the case of administration to dogs, the compositions according to the invention will contain 2 to 8 mg/kg of Tramadol and approx. 0.5 to 4 mg/Kg of Firocoxib, preferably 1 to 4 mg/Kg, and more preferably 2 to 3 mg/Kg.

Currently, the clinical use of the molecules to which the invention relates by separate administration allows a therapeutic approach designed either to eliminate pain symptoms (Tramadol) or to eliminate pain symptoms and at the same time reduce the extent of the inflammatory process (Firocoxib). It is very important to bear in mind that both molecules are characterised by a close dose-effect relationship, in view of the possible side effects which may arise with a dose increase. It should be emphasised that while Tramadol performs its analgesic function without any particular risk of side effects, even at the full dose, the use of Firocoxib can involve a high risk of serious side effects affecting various organs and systems which, in the worst cases, can lead to the animal's death. It would therefore be very useful in veterinary practice to have a pharmaceutical preparation which allows the therapeutic objective (anti-inflammatory+analgesic) to be attained as far as possible, while minimising the risk of onset of side effects.

Laboratory research conducted by the Applicant on rats has clearly demonstrated that while separate administration of the individual molecules of Tramadol and Firocoxib at different doses shows close dose-effect relationships, their combined administration shows a surprising, unexpected therapeutic activity at doses of Firocoxib below the efficacy threshold tested and recognised as the minimum effective anti-inflammatory dose. The combination according to the invention therefore produces a desired clinical effect, namely an analgesic and above all an anti-inflammatory effect, comparable with that obtained after administration of the full dose of Firocoxib, but using Firocoxib at far lower doses, with a consequent very significant reduction in the risk of onset of side effects, including serious ones, associated with it, thus favourably altering the risk/benefit ratio of the new preparation.

Moreover, the combination of these two molecules also shows a greater effect than that deriving from the sum of the effects obtained after separate administration of the individual components of the combination. This synergic effect means that significant anti-inflammatory and painkilling activity can be obtained despite the reduction in the usual dose of NSAIDs, thus reducing the onset and extent of the known side effects of NSAIDs (gastrointestinal and renal effects, etc.).

Consequently, the combination of Tramadol and Firocoxib according to the invention constitutes an invaluable therapeutic aid which can be used in the treatment of pain and inflammatory processes of all kinds and levels of severity, for both acute and chronic disorders, allowing the usual dose of NSAIDs to be reduced while still obtaining full anti-inflammatory activity, but with a consequent significant reduction in the likelihood of side effects of NSAIDs.

The possibility of obtaining a significant anti-inflammatory effect while reducing the dose of this medicament is of particular importance in the case of dogs and cats, which are very sensitive to the adverse effects of NSAIDs. A reduction in the dose of Firocoxib further increases the safety of the combination according to the invention.

Moreover, as the disorders that require analgesic and anti-inflammatory treatment are very often chronic, long-term treatment with Firocoxib alone has the drawback of increasing the probability of side effects, which in practice limits its use for long periods. Conversely, a medicament deriving from the combination according to the present invention would allow more effective, safer anti-inflammatory and painkilling treatment, which could also be used in the long term.

The combination according to the present invention could be used for:
- analgesic/anti-inflammatory treatment of soft tissue disorders (both acute and chronic);
- analgesic/anti-inflammatory treatment of disorders of the musculoskeletal system (both acute and chronic);
- analgesic/anti-inflammatory treatment in the peri-surgical (pre-surgical, surgical and post-surgical) sphere.

The combination according to the present invention will be used to treat painful inflammatory conditions of the musculoskeletal system, the soft or hard tissues, joint disease, arthritis, osteoarthritis, gouty arthritis, myositis, tendinitis, sequelae of trauma, pain of any origin, including cancer pain, mastitis and equine colic, in pets, especially dogs, cats and horses.

The compositions will be formulated suitably for oral administration. Examples of compositions for oral administration are: water-dispersible tablets, palatable tablets, palatable boluses, oral gels or pastes, drops.

BRIEF DESCRIPTION OF FIGURE

The annexed FIGURE shows the anti-inflammatory activity of Tramadol and Firocoxib alone or combined. The intensity of the oedema, measured with a plethysmometer, is shown as the algebraic difference between the inflamed paw and the normal paw (ml).

PHARMACOLOGICAL TESTS

A study has been conducted to evaluate the effect of combining a very low dose of Firocoxib, with no anti-inflammatory efficacy, and an analgesic dose of Tramadol.

An inflammation model extensively used and validated in the rat was used for the study.

Experimental Protocol

Animals

Sprague-Dawley rats weighing 200-250 grams were used. The animals were housed in groups of 4 to a cage, at the temperature of 22° C.±2° C., with a light-dark cycle of 12/12-hour and unlimited access to food and water. The animals were used after a week's acclimatisation in the housing facility. Each test group consisted of 8 rats.

Inducement of Inflammation

Inflammation was induced in one limb of the rat by administering a suspension of complete Freund adjuvant (CFA) containing 0.1 mg/0.1 ml of inactivated mycobacterium tuberculosis (H37Ra, ATCC 25177), in paraffin oil and mannide monooleate. The CFA was injected into the plantar surface of the left hind paw of the rat. This method induces reproducible inflammation characterised by oedema and pain.

Medicaments

All the medicaments were administered 3 days after the inflammation was induced with CFA. The Firocoxib was resuspended in a carrier consisting of 0.5% methocel, and administered orally in the volume of 1 ml at the doses of 2.5 and 5 mg/Kg.

The dose of 2.5 mg/Kg was combined with Tramadol at the dose of 4 mg/Kg. Tramadol dissolved in saline was administered by the intraperitoneal route (i.p., 0.2 ml/100 grams of weight) 30 minutes before the Firocoxib. Inflammatory oedema was evaluated 1 hour after the Tramadol, corresponding to 90 minutes after the Firocoxib. This period was selected on the basis of earlier studies which demonstrated that the analgesic effect of Tramadol and the anti-inflammatory effect of Firocoxib were greatest at the full dose. The control animals were treated per os with the carrier, and i.p. with the same volume of saline.

Evaluation of Anti-Inflammatory Effect

The intensity of the oedema was measured on day 3 after intraplantar administration of CFA, 90 minutes after Firocoxib, corresponding to 1 hour after i.p. administration of Tramadol. We chose to evaluate the oedema 3 days after it was induced, because it is largest at this time. The paw swelling (oedema) was evaluated by measuring the volume of both hind paws using a specific instrument, the plethysmometer (7150 plethysmometer, Basile, Comerio, Italy). The results are expressed as the algebraic difference between the volume in ml of the inflamed paw (injected with CFA) and the normal uninflamed paw: the greater the difference, the larger the oedema present.

Statistical Analysis

The values are the mean±SD of 8/10 rats.

The significance of the anti-inflammatory activity was evaluated with the Analysis of Variance (ANOVA) test, followed by the Bonferroni multiple comparison test. ANOVA test is the most suitable statistical test when more than 2 treatment groups are present. It is a restrictive test because it takes account of the variability of all the trial groups.

Results

The table and FIGURE show the intensity of the inflammatory oedema after treatment with Tramadol (4 mg/kg) alone, Firocoxib alone at the dose of 5.0 and 2.5 mg/Kg, and the combination of Tramadol 4 mg/kg+Firocoxib 2.5 mg/Kg.

TABLE

| Treatment 90 min. after Firocoxib p.o. and 60 min. after Tramadol | ml (inflamed paw/ normal paw) |
|---|---|
| Saline | 0.84 ± 0.06 |
| Tramadol 4 mg/kg | 0.80 ± 0.06 |
| Firocoxib 5 mg/Kg | 0.42 ± 0.08* |

TABLE-continued

| Treatment 90 min. after Firocoxib p.o. and 60 min. after Tramadol | ml (inflamed paw/ normal paw) |
|---|---|
| Firocoxib 2.5 mg/kg | 0.83 ± 0.05 |
| Firocoxib 2.5 mg/kg + Tramadol 4 mg/kg | 0.50 ± 0.06*# |

Mean ± SD (6-8 animals)
*= p < 0.01 vs saline
= p < 0.01 vs Firocoxib 2.5 mg/Kg ANOVA+Bonferroni's t-Test for Multiple Comparisons As was to be expected for a centrally-acting analgesic, Tramadol (4 mg/kg) had no anti-inflammatory effect. Firocoxib at the dose of 5.0 mg/kg induced a certain anti-inflammatory effect (approx. 50% inhibition of oedema), but when the dose was halved to 2.5 mg/kg, it completely lost its anti-inflammatory effect. Surprisingly, when the ineffective dose of Firocoxib (2.5 mg/kg) was administered together with Tramadol (4 mg/kg), the anti-inflammatory effect reappeared, demonstrated by the fact that the oedema was significantly reduced. The extent of the anti-inflammatory effect observed with the combination of 4 mg/kg of Tramadol+2.5 mg/kg of Firocoxib is comparable with the effect induced by the higher dose of Firocoxib (5.0 mg/kg).

This study clearly shows that a dose of Firocoxib which is ineffective (because it is low) acquires an unexpected, significant anti-inflammatory activity when administered with an analgesic dose of Tramadol. Consequently, the combination to which the present invention relates produces full anti-inflammatory activity with very low doses of Firocoxib, with a significant reduction in adverse effects on the liver, heart, kidney and gastrointestinal functions and clotting disorders.

The compositions according to the invention can be formulated in a way suitable for oral administration to animals, and will be prepared according to conventional methods well known in pharmaceutical technology, such as those described in "Remington's Pharmaceutical Handbook", Mack Publishing Co., N.Y., USA, using excipients, diluents, filling agents and anti-caking agents acceptable for their final use.

Examples of compositions for oral administration are: water-dispersible tablets, palatable tablets, palatable boluses, oral gels or pastes, drops.

The invention claimed is:

1. Method of treating inflammation in animals in need thereof comprising
   preparing a medicament comprising a combination of Tramadol and Firocoxib;
   administering an effective dose of said combination to said animals, said Firocoxib being administered below a minimum effective anti-inflammatory dose; and
   treating said inflammation in said animals.

2. Method of claim 1, in which the animals are pets, caged birds, rodents, lagomorphs, mustelids, ruminants and swine.

3. Method of claim 2, in which the pets are dogs, cats and horses.

4. Method of claim 1, wherein said effective amounts comprises 2 to 8 mg/Kg of Tramadol and approximately 0.5 to 4 mg/Kg of Firocoxib.

5. Method of claim 1, wherein said effective amounts comprises 2 to 8 mg/Kg of Tramadol and approximately 2 to 3 mg/kg of Firocoxib.

* * * * *